US009750588B1

United States Patent
Harmoush

(10) Patent No.: US 9,750,588 B1
(45) Date of Patent: Sep. 5, 2017

(54) TOOTHBRUSH

(71) Applicant: Michael Harmoush, New Port Richey, FL (US)

(72) Inventor: Michael Harmoush, New Port Richey, FL (US)

( * ) Notice: Subject to any disclaimer, the term of this patent is extended or adjusted under 35 U.S.C. 154(b) by 77 days.

(21) Appl. No.: 14/918,469

(22) Filed: Oct. 20, 2015

(51) Int. Cl.
| | |
|---|---|
| *A46B 9/04* | (2006.01) |
| *A61C 17/34* | (2006.01) |
| *A46B 5/02* | (2006.01) |
| *A61C 17/22* | (2006.01) |
| *A46B 5/00* | (2006.01) |

(52) U.S. Cl.
CPC .......... *A61C 17/349* (2013.01); *A46B 5/0008* (2013.01); *A46B 5/021* (2013.01); *A46B 9/04* (2013.01); *A61C 17/222* (2013.01); *A46B 9/045* (2013.01)

(58) Field of Classification Search
CPC ........... A46B 9/045; A46B 9/04; A46B 9/026; A46B 5/0008; A61C 17/349
USPC .......................................... 15/167.2; D4/105
See application file for complete search history.

(56) References Cited

U.S. PATENT DOCUMENTS

| | | | | |
|---|---|---|---|---|
| 6,115,871 A | * | 9/2000 | Royer | A46B 9/04 15/167.1 |
| D758,081 S | * | 6/2016 | Harmoush | D4/105 |
| 2007/0204417 A1 | * | 9/2007 | Russell | A46B 5/0029 15/167.1 |

FOREIGN PATENT DOCUMENTS

DE            571223 C  *  2/1933   ............. A46B 9/026

* cited by examiner

*Primary Examiner* — Laura C Guidotti
(74) *Attorney, Agent, or Firm* — Gulf Coast Intellectual Property Group

(57) ABSTRACT

A toothbrush configured to provide improved cleaning of the rear surface of the upper and lower central and lateral incisors. The toothbrush includes a handle having a first end and a second end. The handle further includes an upper surface and a lower surface and additionally a middle portion intermediate the first end and second end. Secured to the first end is a first bristle group that is configured to extend downward therefrom. Adjacent to the first bristle group is a divider. The divider include a first surface proximate the first bristle group and a second surface opposite thereto. A second bristle group is secured to the second surface of the divider and extends toward said second end of said handle being perpendicular in orientation to said first bristle group. A recess is formed in the lower surface of the handle above the second bristle group.

13 Claims, 1 Drawing Sheet

TOOTHBRUSH

FIELD OF THE INVENTION

The present invention relates generally to personal hygiene devices, more specifically but not by way of limitation, a toothbrush that is constructed to provide improved cleaning of the teeth.

BACKGROUND

It is common for most people to engage in various hygiene routines on daily basis. These routines range from daily bathing to hair care and care of the teeth. The latter is executed by most people at least twice a day and is important in maintaining oral health care. Regular teeth brushing is critical in the prevention of periodontal disease and tooth decay. The environmental conditions of the human mouth and teeth provide an environment that facilitates the growth of natural microbial growth. A plurality of different types of germs and bacteria are found on the gums and roof of the mouth. These bacteria lead to many types of gum disease and teeth loss if an individual does not regularly engage in proper oral hygiene.

Proper oral hygiene typically consists of regular brushing of the teeth. This task is accomplished utilizing a toothbrush and toothpaste and is typically executed several times a day. Conventional toothbrushes have been known in the art for many decades and consist of a handle having a plurality of bristles grouped at one end. Numerous different types of bristles and toothbrush designs have been attempted over the year but no significant improvement has been accomplished. The plethora of these designs has resulted in varying degrees of bristle stiffness and handle designs but none have shown to be more effective than previous designs.

Accordingly, there is a need for a toothbrush that has an improved design that provides a distinctive and unique handle design as well as a first group of bristles and a second group of bristles that provide cleaning of different surface areas of particular teeth.

SUMMARY OF THE INVENTION

It is the object of the present invention to provide a toothbrush having a first end and a second end wherein the toothbrush further includes a first bristle group and a second bristle group proximate the second end.

Another object of the present invention is to provide a toothbrush that is designed to provide improved cleaning of different surface areas of the teeth wherein the first group of bristles and second bristle group are separated by a wall member.

A further object of the present invention is to provide a toothbrush having a first bristle group and a second bristle group wherein the second bristle group is perpendicular in orientation to the first bristle group.

Still another object of the present invention is to provide a toothbrush designed to provide effective cleaning of the rearward surface of the teeth proximate the front of the mouth such as but not limited to the central and lateral incisors.

An additional object of the present invention is to provide a toothbrush that includes a recessed portion of the handle proximate the second bristle group configured to promote access to the inner surface of certain teeth such as the central and lateral incisors.

Yet a further object of the present invention is to provide a toothbrush operable to provide improved cleaning of the teeth that further includes a pad member secured to the handle proximate the second bristle group.

Another object of the present invention is to provide a toothbrush operable to provide improved cleaning of the teeth that includes a handle having three sections with distinct radius configured to enhance the reach of the toothbrush into the human mouth.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
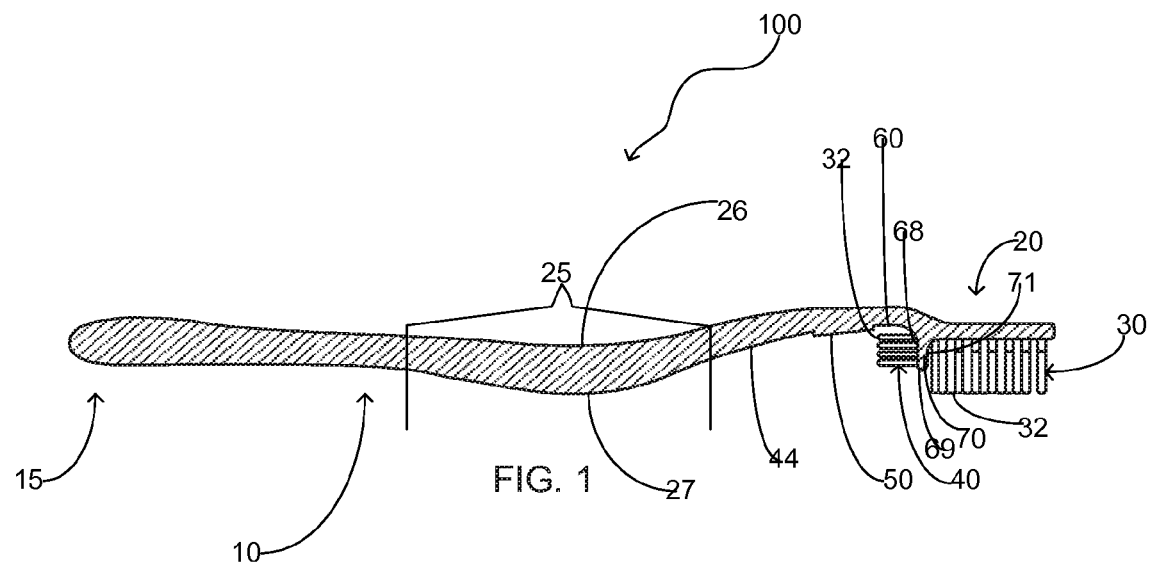
FIG. 1 is a side view of an embodiment of the present invention.
Figure 2:
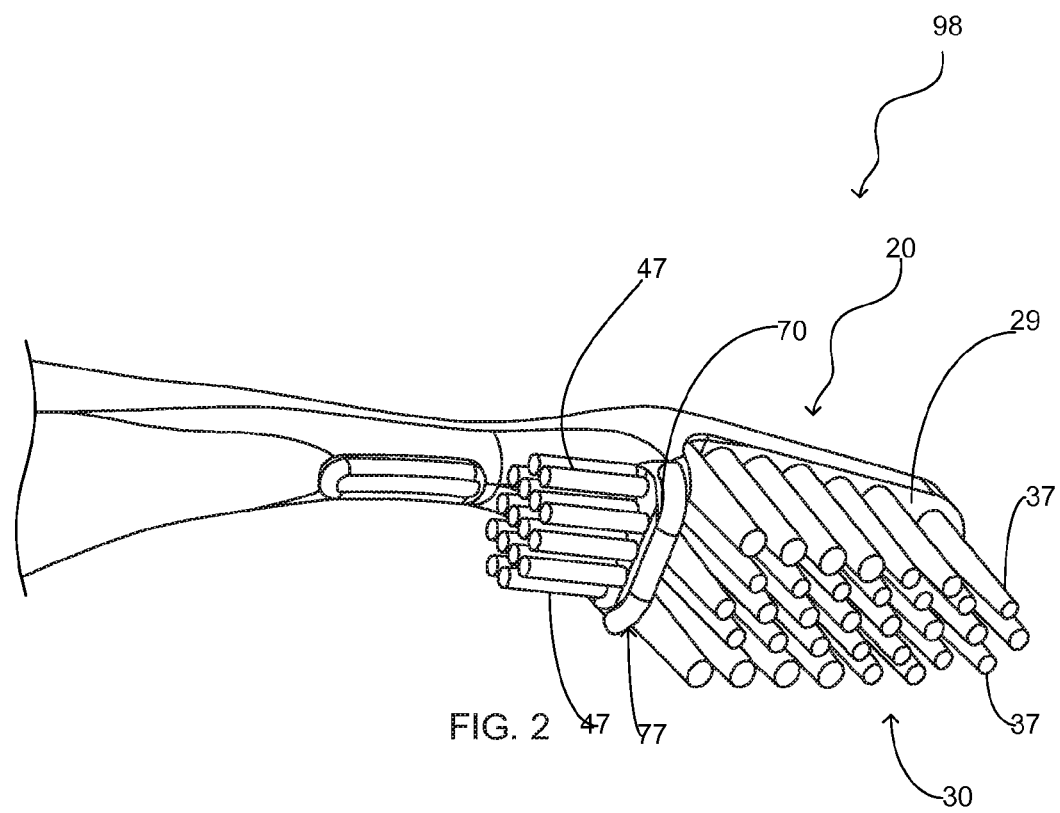
FIG. 2 is a detailed view of the head of the preferred embodiment of the present invention.

Referring now to the drawings submitted herewith, wherein various elements depicted therein are not necessarily drawn to scale and wherein through the views and figures like elements are referenced with identical reference numerals, there is illustrated a toothbrush 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Now referring in particular to FIG. 1 herein, the toothbrush 100 further includes handle 10 having a first end 15 and second end 20. The handle 10 is manufactured from a suitable durable material such as but not limited to plastic. Handle 10 further includes section 25 located intermediate first end 15 and second end 20. Section 25 is manufactured to a specific radius so as to promote positioning of second end 20 within the user's mouth during utilization of the toothbrush 100. Good results have been achieved utilizing a radius of 2.7 inches as measured along surface 26. The aforementioned radius for section 25 promotes axial alignment of lower surface point 27 with ends 32 of first bristle group 30. This axial alignment of the lower surface 27 and ends 32 facilitates the proper positioning of second bristle group 40 to ensure proper positioning for engaging the rear surface of lower and upper central and lateral incisors.

The head 98 illustrated and discussed herein is shown being integrally formed with handle 10. While handle 10 is illustrated and described herein, it is contemplated within the scope of the present invention that numerous different styles of handles could be utilized. More specifically but not by way of limitation, it is contemplated within the scope of the present invention that the head 98 could be secured to an electrically operated handle in addition to a manual handle as shown herein.

Proximate second end 20 is pad 50. Pad 50 is formed on the lower surface 44 of the handle and extends downward therefrom. Pad 20 is operable to provide comfort to a user during utilization of the second bristle group 40. Second bristle group 90 is configured to be perpendicular in orientation to the first bristle group 30. The orientation of the second bristle group 40 provides improved cleaning ability of the rear surface of the upper/lower central and lateral incisors. As is known in the art, saliva ducts are present in the mouth proximate the lower central and lateral incisors. As a result of the proximity of the lower central and lateral incisors to the saliva ducts it is an area that develops plaque and tartar more quickly. Effective cleaning of this area is important to good oral hygiene. As the toothbrush 100 is positioned to place the second bristle group 40 on the rear surface of the upper/lower central and lateral incisors, the pad 50 provides protection for the top edge of the teeth and the lip area during the cleaning of the aforementioned area. The pad 50 is manufactured from a suitable durable material such as but not limited to rubber or gel. It is contemplated within the scope of the present invention that the pad could be manufactured using various different materials and further be provided in alternate sizes in order to accomplish the desired objective as stated herein.

Immediately forward of the pad 50 is recess 60. Recess 60 is formed in the lower surface 44 of the handle 10 utilizing suitable durable techniques. Recess 60 is configured to enhance the ability for the second bristle group 40 to reach the gum-line area of the upper/lower central and lateral incisors. The gum-line area of the aforementioned incisors are a critical area to clean and recess 60 provides the ability for a user to position the second bristle group 40 proximate the gum-line area of the aforementioned incisors. While no particular depth of the recess 60 is required, good results have been achieved utilizing a recess 60 that has a depth of a range between one-eight and one-quarter of an inch.

Extending downward from the first end 20 of the toothbrush 100 is divider 70. Divider 70 is integrally formed with first end 20 utilizing suitable durable techniques and is perpendicular thereto. The divider 70 is manufactured to be a consistent thickness. Having a consistent thickness of the divider 70 intermediate lower end 68 and upper end 69 inhibits any interference with the first bristle group 30. The divider 70 extends downward from the lower surface 44 and is includes a first surface 71 and a second surface 72. Second surface 72 faces towards first end 15 and is configured to have mounted thereon the second bristle group 40. The second bristle group 40 consists of a plurality of nylon bristles or similar suitable material and extend perpendicularly outward from the second surface 72. It is contemplated within the scope of the present invention that the second bristle group 40 could include numerous different quantities of bristles 47 as well as have various arrangements thereof. Integrally formed on divider 70 is second pad 77. Second pad 77 is secured to divider 70 utilizing suitable durable techniques and is manufactured from a suitable material such as but not limited to rubber or gel. Second pad 77 is operable to provide protection for the interior surfaces of a mouth during utilization of the toothbrush 100.

The toothbrush 100 includes a first bristle group 30 that is secured to the lower surface 29 of the first end 20. First bristle group 30 extends downward from said lower surface 29 and is perpendicular thereto. The first bristle group 30 includes a plurality of bristles 37 that are manufactured from a suitable durable material such as but not limited to nylon. It is contemplated within the scope of the present invention that the first bristle group 30 could include numerous different quantities of bristles 37 as well as have various arrangements thereof.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A toothbrush comprising:
   a handle, said handle having a first end and a second end, said handle having an upper surface and a lower surface;
   a head, said head having a first bristle group, said first bristle group being proximate said first end of said handle, said first bristle group including a plurality of nylon bristles, said first bristle group extending downward from said first end;
   said head further including a divider, said divider being proximate said first bristle group distal to said first end, said divider being integrally formed with said handle, said divider extending downward from said first end, said divider being parallel with said first bristle group; said head having a second bristle group, said second bristle group being secured to said divider, said second bristle group being perpendicular to said divider, said second bristle group having a plurality of bristles, said plurality of bristles having a first end and a second end, said second end being distal to said divider;

a recess, said recess being formed in said lower surface of said handle, said recess being located above said second bristle group; and a first pad, said first pad being secured to said handle on said lower surface thereof, said first pad being proximate said second ends of the bristles of said second bristle group.

2. The toothbrush as recited in claim 1, and further including a second pad, said second pad being secured to said divider distal to said handle.

3. The toothbrush as recited in claim 2, wherein said handle is either manual or electric.

4. The toothbrush as recited in claim 3, wherein said divider includes a lower end and an upper end, said divider being a consistent thickness intermediate said lower end and said upper end.

5. The toothbrush as recited in claim 4, wherein said recess in manufactured having a depth within the range of one-eighth of an inch to on-quarter of an inch.

6. A toothbrush configured to have more than one bristle group comprising:

a handle, said handle having a first end and a second end, said handle further including a head proximate said first end, said handle having an upper surface and a lower surface, said handle further including a middle portion intermediate said first end and said second end, said handle being manufactured from a rigid material;

a first bristle group, said first bristle group being proximate said first end of said handle, said first bristle group including a plurality of nylon bristles, said first bristle group extending downward from said lower surface of said handle proximate said first end;

a divider, said divider being proximate said first bristle group distal to said first end, said divider being integrally formed with said handle, said divider extending downward from said first end and being perpendicular thereto, said divider being parallel with said first bristle group, said divider having a first surface and a second surface, said divider having a lower end and an upper end;

a second bristle group, said second bristle group being secured to said second surface of divider and configured to extend towards said second end of said handle, said second bristle group being perpendicular to said divider, said second bristle group having a plurality of bristles, said plurality of bristles having a first end and a second end, said second end being distal to said divider;

a first pad, said first pad being secured to said handle on said lower surface thereof, said first pad being proximate said second ends of the bristles of said second bristle group; and a recess, said recess being formed in said lower surface of said handle, said recess being located above said second bristle group and forward of said first pad.

7. The toothbrush as recited in claim 6, and further including a second pad, said second pad being secured to said upper end of said divider.

8. The toothbrush as recited in claim 7, wherein said divider includes a lower end and an upper end, said divider being a consistent thickness intermediate said lower end and said upper end.

9. The toothbrush as recited in claim 8, wherein said handle is selected from one of the following types of handles: manual or electric.

10. The toothbrush as recited in claim 9, wherein said recess in manufactured having a depth within the range of one-eighth of an inch to on-quarter of an inch.

11. A toothbrush having two bristle groups wherein the toothbrush is configured to provide improved cleaning of the rear surface of central and lateral incisors comprising:

a handle, said handle having a first end and a second end, said handle having an upper surface and a lower surface, said handle further including a middle portion intermediate said first end and said second end, said handle being manufactured from a rigid material;

a first bristle group, said first bristle group being proximate said first end of said handle, said first bristle group including a plurality of nylon bristles, said first bristle group extending downward from said lower surface of said handle proximate said first end;

a divider, said divider being proximate said first bristle group distal to said first end, said divider being integrally formed with said handle, said divider extending downward from said first end and being perpendicular thereto, said divider being parallel with said first bristle group, said divider having a first surface and a second surface, said divider having a lower end and an upper end;

a second bristle group, said second bristle group being secured to said second surface of divider and configured to extend towards said second end of said handle, said second bristle group being perpendicular to said divider, said second bristle group having a plurality of bristles, said plurality of bristles having a first end and a second end, said second end being distal to said divider;

a first pad, said first pad being secured to said handle on said lower surface thereof, said first pad being proximate said second ends of the bristles of said second bristle group;

a recess, said recess being formed in said lower surface of said handle, said recess being located above said second bristle group and forward of said first pad.

12. The toothbrush as recited in claim 11, wherein said divider includes a lower end and an upper end, said divider being a consistent thickness intermediate said lower end and said upper end.

13. The toothbrush as recited in claim 12, wherein said upper surface of said handle at said middle portion is curved in manner having a radius of 2.7 inches.

\* \* \* \* \*